United States Patent
Forber

[11] Patent Number: 5,851,189
[45] Date of Patent: Dec. 22, 1998

[54] TORQUE DEVICE FOR ANGIOPLASTY GUIDEWIRE

[75] Inventor: Simon John Forber, Minneapolis, Minn.

[73] Assignee: B. Braun Medical, Inc., Bethlehem, Pa.

[21] Appl. No.: 651,789

[22] Filed: May 24, 1996

[51] Int. Cl.⁶ ........................................... A61B 5/00
[52] U.S. Cl. ................. 600/585; 600/433; 604/95; 604/280
[58] Field of Search .................... 128/772, 657, 128/658; 604/95, 280, 96, 281, 282, 283

[56] References Cited

U.S. PATENT DOCUMENTS

| | | |
|---|---|---|
| 4,726,369 | 2/1988 | Mar . |
| 4,957,117 | 9/1990 | Wysham . |
| 5,161,534 | 11/1992 | Berthiaume ............................ 128/657 |
| 5,219,332 | 6/1993 | Nelson et al. . |
| 5,312,338 | 5/1994 | Nelson et al. . |
| 5,325,746 | 7/1994 | Anderson ................................. 128/657 |
| 5,392,778 | 2/1995 | Horzewski . |
| 5,423,331 | 6/1995 | Wysham . |

*Primary Examiner*—Max Hindenburg
*Assistant Examiner*—Pamela L. Wingood
*Attorney, Agent, or Firm*—Skinner and Associates

[57] ABSTRACT

A torque device for attaching to and selectively gripping and releasing a catheter guidewire to permit rotational and longitudinal manipulation of the guidewire to steer the guidewire through a vessel. A spindle is threadably engaged in a cap, and a bore through the spindle aligns with a bore through the cap to accept the guidewire. The end of the spindle inside the cap has a pair of fingers straddling the guidewire. As the cap and spindle are rotated with respect to each other, the threaded engagement of the spindle and cap forces the end of the fingers to advance along a tapering bore in the cap, which causes the fingers to close and grip the guidewire. Reversing the direction of rotation releases the grip on the guidewire.

20 Claims, 3 Drawing Sheets

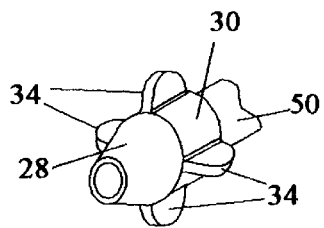 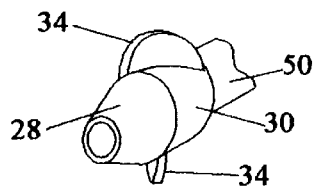 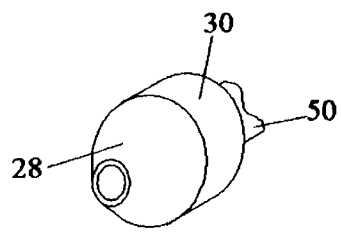
FIG. 9A    FIG. 9B    FIG. 9C
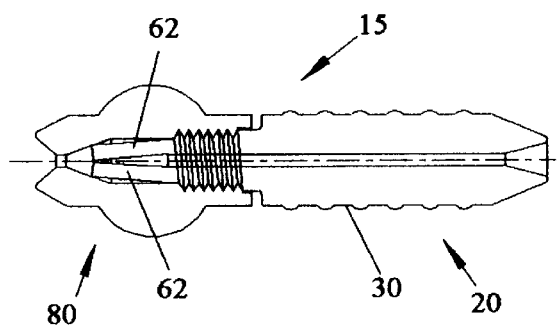
FIG. 10
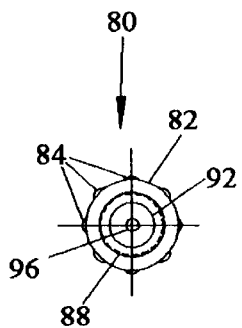 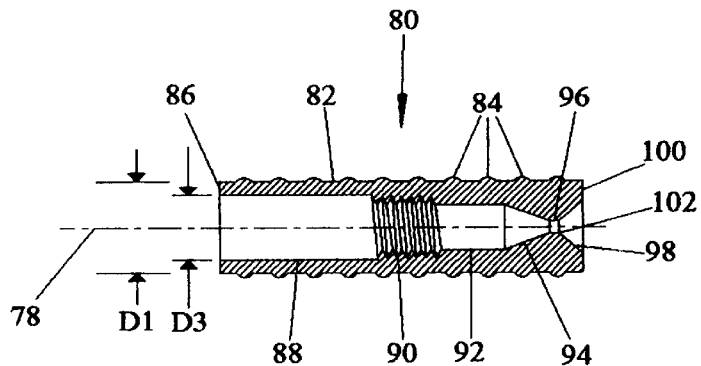
FIG. 6    FIG. 7

TORQUE DEVICE FOR ANGIOPLASTY GUIDEWIRE

BACKGROUND OF THE INVENTION

1. Field of the Invention

The present invention relates, generally, to medical devices. More particularly, the invention relates to radiology and cardiology devices. The device of the invention has particular utility in steering a guide wire used in angioplasty and other procedures.

2. Background Information

The use of guidewires in catheterization and angioplasty procedures is well known. Exemplary descriptions of such use are provided in U.S. Pat. Nos. 5,423,331 and 4,957,117 to Wysham. The distal end of a guide wire typically has an angled tip which can be oriented to help steer the guidewire through curves and junctions of the vasculature of a patient. The orientation of the angled tip is achieved by torqueing the guidewire so that it rotates about its axis. However, since the guidewire has a small diameter and typically a smooth surface, it is not readily torqued by an operator's fingers. Torqueing requires the aid of a larger diameter torque device which is attached to the guide wire.

The most common of the prior art torque devices are referred to as pin-vise devices. Such devices have a structure somewhat similar to a miniature drill chuck with a cylindrical handle. Those devices typically have three parts: a cylindrical handle, a threaded tapered cap, and a brass collet. The cap is screwed down over the collet, which has a plurality of fingers that move radially inward to grip a guidewire running through the collet. The proximal end of the guidewire is threaded through the pin-vise device, and the pin-vise device is then advanced to a desired location, which is typically 2–3 centimeters from the hub of a catheter, to achieve the desired control of the guidewire. The cap is rotated with respect to the handle, which tightens the collet and grips the wire. The torque device must be loosened and repositioned on the guidewire every time the guidewire is advanced 2–3 centimeters.

Among the disadvantages of the pin-vise devices are that they have three parts, one of which, the collet, must be provided in two sizes to accommodate the full range of guidewire sizes that typically range from 0.010 to 0.038 inch diameter. A further disadvantage of the pin-vise devices is that the collet is relatively short and, since it has a plurality of fingers, it also has a plurality of slots between the fingers. This configuration makes the guidewire susceptible to being pinched in one of those slots rather than being centered in the collet. Such pinching could kink the guide wire, requiring it to be removed and replaced.

Other torque devices are designed to be installed on the guidewire by slipping the guide wire through a slot in the device rather than threading it through the center of the device. One such device is disclosed in U.S. Pat. No. 4,726,369 to Mar. Mar's device is simply a cylindrical section of rubber with a slot in it to accept the wire and a plastic sleeve near each end of the rubber cylinder to hold the slot closed against the guidewire. To move the device, the wire is simply pulled out of the slot and the device reinstalled at a different location on the wire. While Mar's device is simple, such a device may not provide enough grip on the guide wire, especially after repeated removal and installation of the device. To achieve greater grip, the operator must manually squeeze the rubber section between the sleeves.

A more complex version of the slot-and-rubber torque device is disclosed in U.S. Pat. Nos. 5,219,332 and 5,312,338 to Nelson et al. Nelson's device uses two mating cylindrical sections which each have a slot which can be aligned to accept the guide wire. When the cylindrical sections are together and the slots are aligned, an internal recess in the cylindrical sections accepts a dog-bone shaped rubber element which holds the two cylindrical sections together as well as grips the wire. With the rubber element installed, and the slots aligned, the device is installed on the guide wire and the two cylindrical sections are rotated with respect to each other, which twists the rubber element around the guide wire to grip it. Detents provide two rotational positions, one to keep the device on the wire but allow it to slide, and another to tightly grip the wire. As with the Mar device, the gripability of the device is a function of the friction between the rubber and the wire. As the rubber gets worn, or stretched, or wet, it can lose its ability to adequately grip the wire.

Disadvantages of torque devices which use rubber to grip the wire can be overcome by devices which use mechanical mechanisms to more positively grip the wire, but these too have disadvantages. A slotted device which uses a spring loaded mechanism rather than rubber to grip the wire is disclosed in U.S. Pat. No. 4,829,999 to Auth. This device is very simple, and use of the device is much like clamping a clothespin on a clothesline. However, the device can easily be dropped, making it unsterile and requiring replacement.

U.S. Pat. No. 4,858,810 to Intlekofer et al. discloses a slotted device with a longitudinally sliding mechanism in the slot to grip the guidewire. Besides being more complex than the Auth device, it suffers from the same problems as the Auth device and is somewhat more cumbersome to place on the guidewire.

Another approach to torque devices is disclosed in U.S. Pat. Nos. 4,957,117 and 5,423,331 to Wysham. The devices discussed above require two hands to tighten and loosen the device. Wysham's devices may be operated with just one hand. As with the pin-vise devices, the guide wire is threaded through the center of these devices rather than installed in a slot. Compared to the other devices described above, these devices are more complex and have a gripping mechanism which moves transversely in a large recess in a cylindrical body. The gripping member is supported by a leaf spring. When the gripping member is depressed, gripping faces on the gripping member press the guidewire against the bottom wall of the recess in the cylindrical body. A latch mechanism locks the gripping member in place until release levers are depressed, which allow the leaf spring to move the gripping mechanism away from the guidewire. The complexity of these devices make them relatively expensive to produce.

Despite the need in the art for a torque device which overcomes the disadvantages, of the prior art, none insofar as is known has been developed. Accordingly, it is an object of the present invention to provide an improved torque device which provides adequate and adjustable gripping force on the guidewire regardless of the condition of the wire or its diameter. It is a further object of this invention to provide a torque device which can accommodate the full range of guide wire diameters with a single device. It is a further object to provide a torque device which centers the guidewire in the device thereby preventing it from kinking due to misalignment. It is a further object to provide a torque device having a low number of parts that are simple and relatively inexpensive to produce.

BRIEF SUMMARY OF THE INVENTION

The apparatus of the present invention provides a torque device for attaching to and selectively gripping and releasing a catheter guidewire to permit rotational and longitudinal manipulation of the guidewire to steer the guidewire through a a blood vessel such as an artery. The device has fewer parts than prior art devices, is less likely to kink the guidewire, and has the ability to accommodate all the diameters of guidewires typically used in catheters.

The torque device is comprised of two parts, namely a spindle and a cap, which threadably engage each other. In the preferred embodiment, the distal end of the spindle has a larger diameter cylindrical portion which extends beyond the cap when the spindle and cap are assembled. There are features on the outside surface of that cylindrical portion of the spindle to aid in manually rotating the spindle with respect to the cap. In the preferred embodiment, these features are a pair of diametrically opposed longitudinal tabs extending perpendicularly from the cylindrical section. Other structures such as knurls, ridges, or a textured pattern may also work. In another embodiment, the features are four longitudinal tabs extending perpendicularly from the cylindrical section located at 90° increments around it. In yet another embodiment, the features are a pair of diametrically opposed tabs extending from the cylindrical section, which tabs are not aligned with the longitudinal axis of the spindle. In still another embodiment, instead of tabs, the cylindrical section is of a larger diameter and may have a textured surface. The features of these alternate embodiments may better facilitate one-handed operation of the torque device.

In the preferred embodiment, extending proximally from the larger cylindrical portion of the spindle is a smaller diameter cylindrical portion having external threads over at least a portion of it. Extending proximally from the smaller cylindrical portion, in the preferred embodiment, are a pair of diametrically opposed fingers. The fingers are separated by a slot aligned with a bore passing through the longitudinal axis of the spindle. In the preferred embodiment, the width of the slot and the diameter of the bore are approximately the same.

The cap has a bore large enough to accept the smaller diameter cylindrical portion of the spindle and also has internal threads which mate with the external threads on the spindle. Near the proximal end of the cap, the bore tapers proximally to a smaller diameter which is approximately the same diameter as the bore of the spindle.

When the cap and spindle are assembled, the small bore in the cap aligns with the bore and slot in the spindle. The guidewire passes through the bore and slot in the spindle and the small bore in the cap. As the cap and spindle are rotated with respect to each other, the threaded engagement of the spindle and cap forces the end of the fingers of the spindle to advance along the tapering bore in the cap, which causes the fingers to close and grip the guidewire. Reversing the direction of rotation releases the grip on the guidewire.

In the preferred embodiment, the thread pitch is such that approximately 180° of relative rotation of the spindle and cap cycles the device between secure grip and release of the guidewire. The tightness of the grip can be adjusted simply by further rotating the two parts.

In the preferred embodiment, the cap is significantly longer than the portion of the spindle extending beyond it. When the device is installed on a guide wire, the cap functions as a handle to manually manipulate the device to rotate and slide the guide wire in a catheter. In an alternate embodiment, the direction of the elements is reversed, the cap is relatively short, and the portion of the spindle extending beyond the cap is longer than in the preferred embodiment. With this embodiment, the portion of the spindle extending beyond the cap functions as the handle. Either of these embodiments can be installed in either direction on the guide wire and still function effectively.

The features, benefits and objects of this invention will become clear to those skilled in the art by reference to the following description, claims and drawings.

BRIEF DESCRIPTION OF THE SEVERAL VIEWS OF THE DRAWING

FIG. 6 is an end view of the cap of FIG. 1.

FIG. 7 is a sectional view taken along line 7—7 in FIG. 1.

FIGS. 9A, 9B and 9C are perspective views of portions of alternate embodiments of the spindle.

FIG. 10 is a cross sectional view of an alternate embodiment of the torque device.

DETAILED DESCRIPTION

Figure 8:
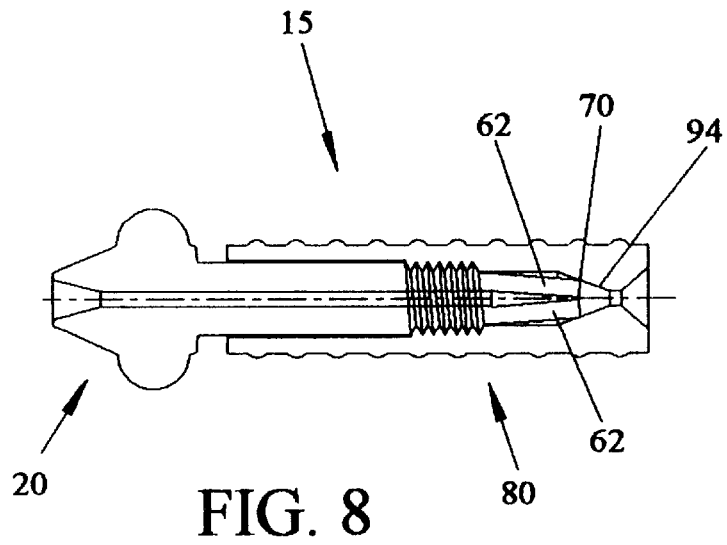
FIG. 8 is a side view, partially in crossection, of the assembled torque device.

Referring to FIGS. 1–8, a preferred embodiment of the present invention is illustrated and generally indicated by the reference numeral 15. For clarity, the relative position of elements are described using proximal and distal designations. However, the orientation of torque device 15 on a guidewire 16 can be reversed without diminishing the function or performance of the device. Torque device 15 is comprise of two parts: a spindle 20 and a cap 80.

Figure 4:
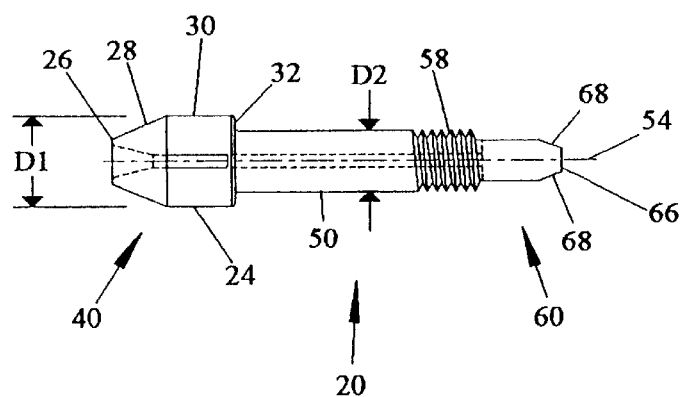
FIG. 4 is a top view of the spindle of FIG. 1.

Refering particularly to FIG. 4, spindle 20 has a head 24 of larger diameter D1 at distal end 40, a pair of fingers 62 at proximal end 60, a center cylindrical section 50 of smaller diameter D2 located between head 24 and fingers 62, and a bore 52 along longitudinal axis 54 of spindle 20. In the preferred embodiment, bore 52 is approximately 0.040 inches diameter, D1 is approximately ¼ inch, D2 is approximately 0.2 inches and the length of spindle 20 is approximately 1.5 inches.

Head 24 has a distal tip 26, a conical section 28 extending from distal tip 26 proximally approximately half of the length of head 24, and a cylindrical section 30 extending proximally from conical section 28 to proximal face 32 of head 24. Proximal face 32 blends into cylindrical section 50. Although it is not necessary for cylindrical section 30 to have any features for torque device 15 to properly function, in the preferred embodiment cylindrical section 30 has features 34 which facilitate manual gripping and rotating of head 24 to lock and unlock torque device 15. In the preferred embodiment, features 34 are a pair of diametrically opposed longitudinal tabs extending perpendicularly from cylindrical section 30. Other structures such as knurls, ridges, or a textured pattern may also be used.

Referring to FIG. 9A, in another embodiment features 34 are four longitudinal tabs extending perpendicular from cylindrical section 30 located at 90° increments around cylindrical section 30. Referring to FIG. 9B, in yet another embodiment features 34 are a pair of diametrically opposed tabs extending from cylindrical section 30, but the tabs are not aligned with longitudinal axis 54. Referring to FIG. 9C, in yet another embodiment, rather than having tabs, cylindrical section 30 is of larger diameter and may have a textured surface. The features of these three embodiments may better facilitate one-handed operation of torque device 15.

Figure 5:
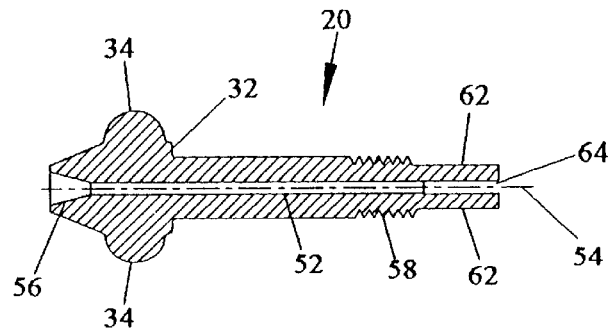
FIG. 5 is a sectional view taken along line 5—5 in FIG. 1.
Figure 2:
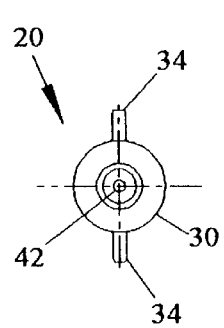
FIG. 2 is an end view of the spindle of FIG. 1.
Figure 3:
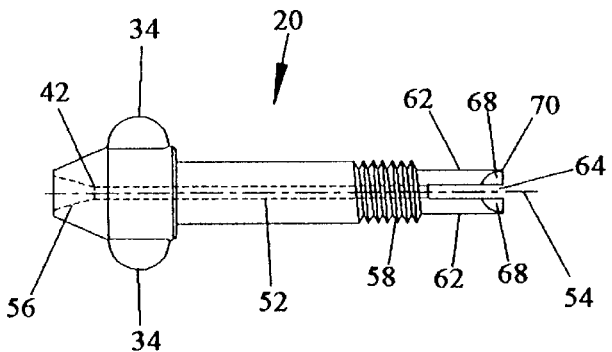
FIG. 3 is a side view of the spindle of FIG. 1.

Referring to FIGS. 3–5, bore 52 has an enlarged tapering section 56 which extends from distal tip 26 of head 24 proximally approximately ⅛ inch in the preferred embodiment. This tapered section 56 of bore 52 facilitates threading the guidewire (not shown) into the distal end of torque device 15. Tapered section 56 also provides a transition from bore 52 so that edge 42 is not so sharp as to cause damage to the guidewire if the guidewire extending beyond torque device 20 is pulled sideways with respect to the longitudinal axis 54.

Center cylindrical section 50 has external threads 58 at its proximal end. In the preferred embodiment the length of threads are approximately ¼ inch.

Proximal end 60 of spindle 20 has a plurality of fingers 62 extending proximally from threads 58. In the preferred embodiment, the number of fingers 62 is two and they are diametrically opposed with respect to longitudinal axis 54. The configuration having two diametrically opposed fingers is the best for accommodating the widest range of guidewire diameters with the same device, and for minimizing the chance that the guidewire would be misaligned with respect to the fingers and be pinched improperly and possibly kinked if there were more than two fingers. Fingers 62 are separated by slot 64 which is approximately the same width as bore 52 and extends from proximal tip 66 to threads 58 along axis 54 and passes transversely all the way through proximal end 60 of spindle 20. Fingers 62 have generally planar tapers 68 extending from their tips 66 distally nearly half of the length of fingers 62. This taper is to allow clearance for fingers 62 in the direction of slot 64 when spindle 20 engages cap 80 and an internal taper in cap 80 compresses fingers 62.

Figure 1:
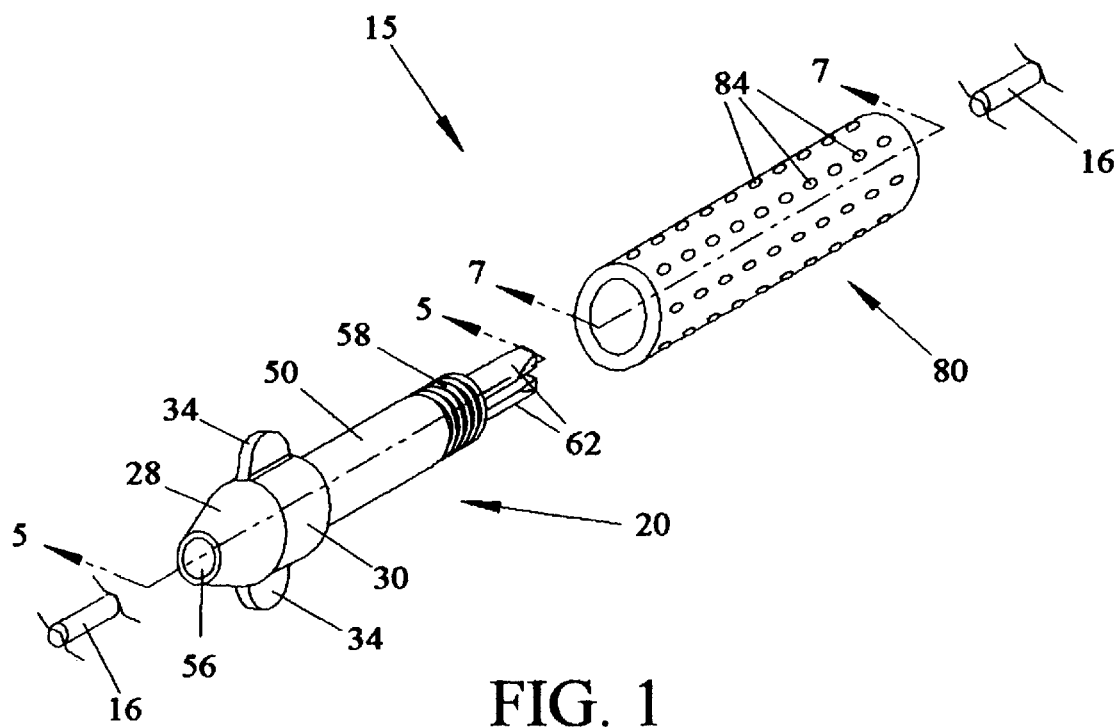
FIG. 1 is a perspective view of the preferred embodiment of the torque device disassembled into its two parts, the spindle and the cap.

Referring to FIGS. 1, 6 and 7, cap 80 is cylindrical having an external diameter D1 which, in the preferred embodiment is approximately the same as diameter D1 of spindle 20. Although it is not necessary for the external surface 82 of cap 80 to have any features for device 15 to properly function, in the preferred embodiment, external surface 82 of cap 80 has features 84 which facilitate manual gripping and rotating of cap 80 to lock and unlock torque device 15. In the preferred embodiment, features 84 are a series of bumps spaced uniformly axially and circumferentially around external surface 82 of cap 80. Other structures such as depressions, knurls, ridges, or any textured pattern may work as well for features 84.

Cap 80 has an internal bore 88 extending along central axis 78 from distal tip 86 proximally for a distance nearly that of the length of center cylinder section 50 of spindle 20 from head 24 to threads 58. Bore 88 is of diameter D3 sufficiently large to allow clearance for center cylinder section 50 when cap 80 and spindle 20 are engaged.

Internal threads 90 extend from bore 88 proximally for a length corresponding to the length of threads 58 on spindle 20. Internal threads 90 in cap 80 mate with external threads 58 of spindle 20 when spindle 20 and cap 80 are engaged.

Cylindrical bore 92 extends from threads 90 proximally for a length less than the length of fingers 62 on spindle 20. Conical bore 94 extends from cylindrical bore 92 and is of a length such that the total length of cylindrical bore 92 and conical bore 94 is approximately the same length as fingers 62 of spindle 20. When cap 80 and spindle 20 engage, conical bore 94 contacts edge 70 at tip 66 of fingers 62 closing slot 64 and forcing fingers 62 to grip the guidewire (not shown). Conical bore 94 also directs the proximal end of the guidewire (not shown) from cylindrical bore 92 into cylindrical bore 96 if cap 80 is installed onto the guidewire separately from spindle 20.

Cylindrical bore 96 extends proximally from conical bore 94 for a short distance. In the preferred embodiment, cylindrical bore 96 is the same diameter as bore 52 in spindle 20. Bore 96 centers the guidewire in torque device 15 and assures that the guidewire is properly positioned between fingers 62 of spindle 20.

A conical bore 98 extends proximally from bore 96 to proximal end 100 of cap 80. Conical bore 98 facilitates threading of the guidewire (not shown) into the proximal end of torque device 15. Conical bore 98 also provides a transition from bore 96 so that edge 102 is not so sharp as to cause damage to the guidewire if the guidewire extending beyond torque device 20 is pulled sideways with respect to the longitudinal axis 54.

Referring to FIGS. 5, 7, and 8, in use, device 15 is assembled by installing cap 80 on spindle 20 so that internal threads 90 of cap 80 engage external threads 58 of spindle 20. The proximal end of a guidewire (not shown) is inserted into torque device 15 through tapered bore 56 of spindle 20 and pushed through bore 52 and slot 64 of spindle 20, and bore 96 of cap 80 where it exits torque device 15 through tapered bore 98. Because of the relatively long center cylindrical section 50 of spindle 20, the guidewire is centered in the spindle 20 and does not tend to move sideways as it passes through slot 64. The alignment of bore 96 of cap 80 with bore 52 and slot 64 of spindle 20 also keeps the guidewire centered in slot 64. In addition to the alignment of bore 96 of cap 80 with bore 52 and slot 64 of spindle 20, tapered bore 94 helps direct the end of the guidewire into bore 96 as the guidewire is threaded through torque device 15.

It is also possible to install the guidewire in torque device 15 by inserting the distal end of a guidewire into tapered bore 98 of cap 80 then push it through bore 96 of cap 80, slot 64 and bore 52 of spindle 20 where it exits the distal end 40 of device 15 through tapered bore 56 of spindle 20. While the alignment of bore 96 of cap 80 with slot 64 and bore 52 of spindle 20 allows installing of the guidewire from this direction, usually the distal end of the guidewire is much more flexible than the proximal end or it has a J-tip on it which makes threading the proximal end through torque device 15 more practical.

Referring to FIG. 8, torque device 15 is slid to the desired location on the guidewire, then cap 80 is manually rotated with respect to spindle 20 so as to cause conical bore 94 of cap 80 to contact edge 70 at tip 66 of fingers 62 of spindle 20. As cap 80 is further rotated with respect to spindle 20, edge 70 travels along conical bore 94, thereby reducing the width of slot 64 and forcing fingers 62 to grip the guidewire (not shown). Cap 80 is rotated with respect to spindle 20 until the desired grip on the guidewire is achieved. The torque device can then be rotated as a unit to rotate the guidewire as needed. If a tighter grip is needed, the cap 80 is simply rotated more with respect to spindle 20.

To release the guidewire, the cap is simply rotated the opposite direction. Torque device 15 can then be slid to a new position on the guidewire and tightened again. The pitch of threads 58 and 90 are such that device 15 can be cycled between free sliding and a sufficiently tight grip on the guidewire to rotate the wire by rotating cap 80 and spindle 20 approximately 180° with respect to each other.

Because there are only two fingers 62 on spindle 20, torque device 15 can accommodate the entire typical range of diameters (0.015 to 0.038 inches) typically used for guidewires with the same device. A single torque device can securely grasp guidewires having a diameter ranging from 0.009 to 0.038 inches. In contrast, known commercially available torque devices of a cylindrical form that use fingers and a conical ramp to grip wires usually come in two sizes. One size accommodates wires having diameters ranging from 0.010 to 0.018 inches and the other size accommodates wires having a diameter ranging from 0.018 to 0.038 inches. Fingers 62 close more for the small diameters and less for the larger diameters. Cap 80 is simply advanced on spindle 20 until grip is achieved, regardless of wire diameter.

The configuration of the preferred embodiment having two longitudinally aligned tabs 34 on head 24 of spindle 20 is designed to primarily be operated with two hands. Typically one hand of the person inserting the guidewire in a catheter is holding the hub of the catheter and the other hand is manipulating the guidewire by manipulating the torque device. Since the torque device is typically located on the guidewire 2–3 centimeters from the hub of the catheter, the operator's two hands are always in close proximity of each other.

One-handed operation of torque device 15 is possible by gripping cap 80 between the thumb and middle finger and rotating spindle 20 using the index finger on head 24. Tabs 34 on head 24 are well suited for interacting with the pad of the index finger when rotating head 24 with the index finger. An embodiment of device 15 having more than two tabs 34, as shown in FIG. 9A, or two tabs not longitudinally aligned, as shown in FIG. 9B, or a larger diameter cylindrical section 30 with a textured surface rather than tabs as shown in FIG. 9C would be better suited for one-handed operation.

In the preferred embodiment, the cap 80 is significantly longer than the portion of the spindle extending beyond it. When the device 15 is installed on a guidewire, the cap functions as a handle to manually manipulate the device to rotate and slide the guidewire in a catheter. Referring to FIG. 10, in an alternate embodiment, the direction of the elements is reversed, cap 80 is shorter than in the preferred embodiment and the cylindrical portion 30 of the spindle 20 extending beyond cap 80 is longer than in the preferred embodiment. With this embodiment, the portion of the spindle extending beyond the cap functions as the handle. Either of these embodiments can be installed in either direction on the guidewire and still function effectively.

The torque device of the present invention overcomes the disadvantages of the prior art devices by providing a torque device which can apply adequate and adjustable gripping force on the guidewire regardless of the condition of the wire or its diameter. A single device can accommodate the full range of guidewire diameters currently used. The guidewire is kept centered in the device thereby preventing it from kinking due to misalignment. This device is designed to operate easily and reliably, and its two parts are relatively simple and inexpensive to produce.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. A device for steering a guidewire having a diameter within the commercially available range of 0.009 to 0.038 inches, comprising:
   (a) a spindle having a body section having external threads, an axial bore in said body section for receiving said guidewire, and two fingers extending from one end of said body section;
   (b) a cap having an axial bore for receiving said spindle, said bore having internal threads cooperating with said external threads of said spindle, said bore having a tapered portion adapted for engaging and closing said fingers of said spindle when said spindle and said cap are screwed together;
   (c) said spindle and said cap screwing together to advance said fingers along said tapered portion and to rotate and close said fingers of said spindle around said guidewire, and further screwing apart to retract said fingers along said tapered portion and to rotate and open said fingers; and
   (d) said rotating fingers being diametrically opposed and having a form to securely grip any of said commercially available guidewires in between said fingers.

2. The device of claim 1 wherein:
   (a) said body section of said spindle further comprises a longitudinal axis, a center section, and a head section having a tip;
   (b) said bore of said spindle has a diameter sufficient to receive a guidewire, and extends from said tip along said longitudinal axis through said head section and said center section;
   (c) said fingers extend axially from said center section and have tips;
   (d) said cap further comprises an external surface, a first end, a second end, and a longitudinal axis;
   (e) said bore of said cap is along said longitudinal axis and further comprises
      (i) a first section of sufficient diameter to receive said center section of said body section of said spindle, said first section having said internal threads, said first section extending from said first end;
      (ii) a second section extending from said first section, said second section having said tapered portion; and
   (g) when said spindle is threadably engaged with said cap, said head section of said body of said spindle extends beyond said first end of said cap.

3. The device of claim 2 wherein said head section of said spindle has a larger diameter than said center section.

4. The device of claim 3 further comprising an external conical taper on at least a portion of said head section.

5. The device of claim 2 wherein said portion of said head section of said spindle has at least one feature to aid in rotating said spindle with respect to said cap.

6. The device of claim 5 wherein said at least one feature is a pair of tabs diametrically opposed on and extending radially out from said head section of said spindle.

7. The device of claim 6 wherein said tabs are longitudinally aligned with said longitudinal axis of said spindle.

8. The device of claim 5 wherein said at least one feature is a plurality of tabs extending radially out from and uniformly spaced around said head section of said spindle.

9. The device of claim 5 wherein said at least one feature is a textured surface.

10. The device of claim 2 wherein a portion of said bore of said spindle has a conically expanding taper to said first tip.

11. The device of claim 2 wherein said fingers are tapered near said tips such that said tapering facilitates closing and opening of said fingers when said tips of said fingers advance or retract along said tapered portion of said bore of said cap.

12. The device of claim 2 wherein said bore of said cap further comprises a third section extending from said second section to said second end, said third section having at least a portion which has a diameter substantially smaller than that of said first section.

13. The device of claim 12 wherein said third section of said bore of said cap further comprises a portion with a conically expanding taper to said second end.

14. The device of claim 2 wherein said external surface of said cap has at least one feature to increase friction between said external surface and fingers of a person operating said device.

15. The device of claim 14 wherein said at least one feature is a plurality of bumps arranged on said surface.

16. The device of claim 15 wherein said bumps are uniformly spaced longitudinally and circumferentially on said surface.

17. The device of claim 14 wherein said at least one feature is a textured surface.

18. The device of claim 1 further comprising a longitudinal slot along said longitudinal axis of said spindle between said fingers, said slot extending from said bore.

19. A device for attaching to and selectively gripping and releasing a catheter guidewire having a diameter within the commercially available range of 0.009 to 0.038 inches to permit rotational and longitudinal manipulation of the guidewire to steer the guidewire through a vessel, comprising:

(a) a spindle having, a head section with a tip, a center section having external threads, a longitudinal axis, a bore for receiving the guidewire, said bore extending from said tip along said longitudinal axis through said head section and said center section, said bore having a portion which conically tapers expanding to said tip, a pair of fingers extending axially from said center section, said fingers being diametrically opposed with respect to said longitudinal axis of said spindle, said fingers having tips, a longitudinal slot along said longitudinal axis between said fingers, said slot extending from said bore to said tips of said fingers;

(b) a cap having an external surface with a plurality of bumps uniformly spaced longitudinally and circumferentially on said surface to increase friction between said external surface and fingers of a person operating said device, a first end, a second end, a longitudinal axis, a bore along said longitudinal axis having (i) a first section of sufficient diameter to receive said center section of said spindle, said first section having internal threads which cooperate with said external threads of said spindle, said first section extending from said first end;

(ii) a second section extending from said first section, said second section having at least a portion which tapers to a smaller diameter;

(iii) a third section extending from said second section to said second end, said third section having at least a portion which has a diameter substantially smaller than that of said first section, said third section having a portion with a conically expanding taper to said second end;

(c) wherein when said spindle is threadably engaged with said cap said head section of said spindle extends beyond said first end of said cap, said head section having a larger diameter than said center section of said spindle and a conical taper on at least a portion of said head section, said head section having a pair of tabs diametrically opposed on and extending radially out from said head section and longitudinally aligned with said longitudinal axis of said spindle, said tabs being to aid in rotating said spindle with respect to said cap;

(d) wherein said guidewire passes through said bore and said slot and between said fingers of said spindle and through said third section of said bore of said cap;

(e) wherein said spindle and said cap are rotated relative to each other to selectively cause said tips of said fingers to advance or retract along said tapered portion of said second section of said bore of said cap, thereby causing said fingers of said spindle to selectively close and grip or open and release said guidewire, said fingers being tapered near said tips such that said tapering facilitates said closing and opening of said fingers, and (f) said rotating fingers having a form to securely grip any of said commercially available guidewires in between said fingers.

20. A device for steering a guidewire having a diameter within the commercially available range of 0.009 to 0.038 inches, comprising:

(a) a generally cylindrical spindle including a body section having external threads, an axial bore in said body section for receiving said guidewire, and two fingers extending axially from one end of said body section;

(b) a generally cylindrical cap having an axial bore for receiving said spindle and said guidewire, said bore having internal threads cooperating with said external threads of said spindle, said bore having a tapered portion adapted for engaging and closing said fingers of said spindle, said fingers being tapered to provide rotational clearance between said fingers and said tapered portion of said bore;

(c) said spindle and said cap being capable of screwing apart and screwing together along said external and internal threads, wherein upon being screwed together said fingers rotate and engage said tapered portion, and further close and grip said guidewire, wherein upon being screwed apart said fingers release said guidewire, open and disengage said tapered portion; and (d) said rotating fingers being diametrically opposed and having a form to securely grip any of said commercially available guidewires in between said fingers.

* * * * *